United States Patent [19]

Imai et al.

[11] Patent Number: 4,595,673

[45] Date of Patent: Jun. 17, 1986

[54] DEHYDROGENATION CATALYST COMPOSITIONS AND METHOD OF THEIR PREPARATION

[75] Inventors: Tamotsu Imai, Mount Prospect; Hayim Abrevaya, Chicago, both of Ill.

[73] Assignee: UOP Inc., Des Plaines, Ill.

[21] Appl. No.: 676,444

[22] Filed: Nov. 29, 1984

[51] Int. Cl.$^4$ .................. B01J 21/04; B01J 23/58; B01J 23/62

[52] U.S. Cl. .................. 502/227; 502/330; 585/627

[58] Field of Search ................ 502/227, 330; 585/627

[56] References Cited

U.S. PATENT DOCUMENTS

| | | | |
|---|---|---|---|
| 2,479,109 | 8/1949 | Haensel | 252/442 |
| 2,479,110 | 8/1949 | Haensel | 196/50 |
| 2,930,763 | 3/1960 | Haensel | 252/441 |
| 3,531,543 | 9/1970 | Clippinger et al. | 260/683.3 |
| 3,745,112 | 7/1973 | Rausch | 208/139 |
| 3,892,657 | 7/1975 | Wilhelm | 208/139 |
| 3,909,451 | 9/1975 | Wilhelm | 252/441 |
| 3,996,304 | 12/1976 | Rausch | 260/667 |
| 4,329,258 | 5/1982 | Engelhard et al. | 252/441 |
| 4,363,721 | 12/1982 | Engelhard et al. | 208/139 |
| 4,506,032 | 3/1985 | Imai et al. | 502/227 X |

FOREIGN PATENT DOCUMENTS 1499297 1/1978 United Kingdom .

OTHER PUBLICATIONS

Journal of the American Chemical Society, 82 2471 (1960).

*Primary Examiner*—W. J. Shine
*Attorney, Agent, or Firm*—Thomas K. McBride; John F. Spears, Jr.

[57] ABSTRACT

A novel hydrocarbon conversion catalyst is disclosed. Additionally, a method of preparing the catalyst and a process for its use are disclosed. The catalyst comprises a platinum group component, a Group IVA component and an alkali component on a carrier material. The alkali component further comprises from about 0.05 to about 10.0 wt. %, on the weight of the composite, of a second alkali metal. The catalyst has particular utility as a dehydrogenation catalyst.

17 Claims, 4 Drawing Figures

DEHYDROGENATION CATALYST COMPOSITIONS AND METHOD OF THEIR PREPARATION

BACKGROUND OF THE INVENTION

This invention relates to the conversion of hydrocarbons, especially the dehydrogenation of dehydrogenatable hydrocarbons, in the presence of a catalyst composite. This invention also pertains to a new catalyst composite and a method of making it.

Dehydrogenating hydrocarbons is an important commercial hydrocarbon conversion process because of the great demand for dehydrogenated hydrocarbons for the manufacture of various chemical products such as detergents, high octane gasolines, pharmaceutical products, plastics, synthetic rubbers, and other products well known to those skilled in the art. One example of this process is dehydrogenating isobutane to produce isobutylene which can be polymerized to provide tackifying agents for adhesives, viscosity-index additives for motor oils and impact-resistant and anti-oxidant additives for plastics.

INFORMATION DISCLOSURE

It is well known to catalyze the conversion of hydrocarbons with solid catalysts comprising platinum group metals. For example, U.S. Pat. Nos. 2,479,109 and 2,479,110 disclose a catalyst comprising platinum on alumina with combined halogen for catalyzing reforming, hydrogenating, hydrocracking, oxidizing and dehydrogenating reactions. The term "reforming" in these patents means simultaneously dehydrogenating, isomerizing, cyclizing and cracking a gasoline feedstock. The combined halogen component of this catalyst contributes to a controlled type of cracking activity. The halogen content is preferably maintained below about 8 wt. % of the alumina to avoid excessive side reactions, including cracking reactions, which result in excessive gas formation and low liquid volume yield of reformed products. These patents do not disclose utilizing an alkali component.

U.S. Pat. No. 2,930,763 discloses a two-step process for reforming hydrocarbons. In the first step a hydrocarbon fraction containing unsaturated compounds and/or nitrogen, sulfur or oxygen compounds is contacted with hydrogen in the presence of a catalyst comprising platinum and an alkali metal component on alumina to hydrogenate and saturate the unsaturated compounds and/or reduce the nitrogen, sulfur or oxygen content of the hydrocarbon fraction. In the second step of this process the treated hydrocarbon fraction from the first step is contacted at reforming conditions with a conventional reforming catalyst comprising platinum and combined halogen on alumina. Optionally the catalyst utilized in the first step may contain halogen. A catalyst consisting essentially of alumina, from about 0.01% to about 1% by weight of platinum, from about 0.1% to about 1% by weight of combined halogen, and from about 0.01% to about 1% by weight of an alkali metal is recited in claim 2 of this patent. This patent also does not disclose utilizing a Group IVA component.

U.S. Pat. No. 3,531,543 discloses dehydrogenating hydrocarbons with a catalyst comprising platinum, tin and neutralized metal oxide carrier. The preferred carriers are oxide materials whose intrinsic acidity is substantially neutralized by an alkali or alkaline earth metal component. Pure alumina, for example, has such intrinsic acidity. (cf. Pines and Haag, *Journal of the American Chemical Society*, 82, 2471 (1960)). For example, alumina catalyzed the skeletal isomerization of olefins, dehydrates alcohols and strongly chemisorbs amines. Also, with increasing amounts of alkali present there is a parallel decrease in these acidic alumina properties. Preferably, the carrier of this patent is a non-acidic lithiated alumina. Preferably, the catalysts of this patent are prepared from halogen-free compounds. Compounds containing halogen may be used to manufacture the catalyst provided the halogen residue is efficiently removed from the final catalyst composite.

U.S. Pat. No. 3,745,112 discloses a catalyst for reforming hydrocarbons which comprises a platinum group component, a tin component and a halogen component with a porous carrier material. This patent discloses also that a platinum-tin-alkali or alkaline earth composite is a particularly effective catalyst for dehydrogenating hydrocarbons. In the dehydrogenation catalyst composite of this patent wherein the alkali or alkaline earth component is added, the amount of halogen, if not entirely eliminated, is minimized in order to minimize or neutralize the acidic functions of the alumina and halogen components which tend to promote hydrocarbon cracking and isomerization side reactions which are not desired in commercial dehydrogenation processes.

U.S. Pat. No. 3,892,657 discloses that indium is a good promoter for platinum group-containing catalysts when the atomic ratio of indium to platinum is from about 0.1:1 to about 1:1. This patent discloses also that a Group IVA component selected from the group of germanium, tin, and lead can be added to the acidic form of the indium-containing catalysts for reforming applications. The acidic form of this catalyst, then, comprises a platinum group component, a Group IVA component, an indium component, a halogen component and a porous carrier material. The acidic catalyst contains up to about 3.5 wt. % halogen for reforming applications and up to about 10 wt. % halogen for isomerization and cracking applications. In the dehydrogenation catalyst of this patent wherein the alkali or alkaline earth component is added, however, the halogen content is maintained at the lowest possible value (about 0.1 wt. %).

U.S. Pat. No. 3,909,451 discloses a new method for making a dehydrogenation catalyst comprising a platinum component, a tin component and an alkali or alkaline earth component. In Example V this patent discloses a platinum, tin and potassium composition comprising less than 0.2 wt. % combined chloride.

U.S. Pat. Nos. 4,329,258 and 4,363,721 disclose a catalyst comprising a platinum group metal, tin, an alkali or alkaline earth metal and combined halogen element with a refractory oxide-mineral carrier. The atomic ratio of alkali or alkaline earth metal to platinum group metal for catalysts of these patents is from 0.2 to 10. The patentees discovered that parts-per-million quantities of alkali or alkaline earth component added to catalyst containing a platinum group metal, tin and halogen helped increase the $C_{5}+$ yield in a reforming process.

British Pat. No. 1 499 297 discloses a dehydrogenation catalyst comprising platinum, at least one of the elements gallium, indium and thallium, and an alkali metal, especially lithium or potassium, with alumina as the carrier material. The catalysts of this patent also contain a halogen in an amount of from 0.01 to 0.1 wt. %. The halogen content is purposely reduced to within this low weight % range in order to increase the selectivity and stability of the catalyst.

In the prior art dehydrogenation catalysts acknowledged above comprising a platinum group component, a Group IVA component and an alkali or alkaline earth component wherein the atomic ratio of the alkali or alkaline earth component to the platinum group component is more than 10, then, the halogen component has been eliminated completely or otherwise maintained at the lowest possible level, generally less than 0.1 wt. %, and always less than 0.2 wt. %, calculated on an elemental basis.

U.S. Pat. No. 3,996,304, at column 18, beginning at line 47, discloses a catalytic composite comprising an alumina-containing refractory inorganic oxide, a tin component, a rhodium component, a platinum or palladium component, and an alkali metal component. The alkali metal component is taught as preferably comprising potassium and/or lithium. The catalyst is taught to have specific utility as a selective hydrogenation catalyst for the hydrogenation of conjugated di-olefinic hydrocarbons to mono-olefinic hydrocarbons. Although the reference does disclose that the alkali metal component may comprise potassium and/or lithium, it does not disclose the specific catalyst of the present invention wherein the alkali component comprises from about 0.5 to about 2 wt. %, on the weight of the composite of a first alkali metal, and from about 0.05 to about 3 wt. %, on the weight of the composite of a second alkali metal. As will be hereinafter set forth in the examples the broad teachings relating to the prior art hydrogenation catalyst cannot be considered anticipatory of the novel catalytic composite of the present invention.

Surprisingly, it has been discovered that by incorporating into the catalyst a first and a second alkali metal component there results an improved catalytic composite.

OBJECTS AND EMBODIMENTS

It is, therefore, an object of the present invention to provide an improved catalytic composite and a method of making the same. A corollary objective is to provide an improved process for the conversion of hydrocarbons and especially for the dehydrogenation of hydrocarbons.

Accordingly in a broad embodiment the present invention is a catalytic composite comprising a platinum group component, a Group IVA component and an alkali component on a carrier material wherein the alkali component comprises from about 0.05 to about 2.0 wt. %, on the weight of the composite, of a first alkali metal, and from about 0.05 to about 10.0 wt. %, on the weight of the composite, of a second alkali metal.

In an alternative embodiment the invention is a method of preparing a catalytic composite comprising compositing a carrier material with a platinum group component, a Group IVA component, a first alkali metal sufficient to result in from about 0.05 to about 2.0 wt. %, based on the weight of the composite, and a second alkali metal sufficient to result in from about 0.05 to about 10.0 wt. %, based on the weight of the composite.

In yet another embodiment the invention is a hydrocarbon conversion process comprising contacting a hydrocarbon charge stock with a catalytic composite comprising a platinum group component, a Group IVA component and an alkali component on a carrier material wherein the alkali component comprises from about 0.05 to about 2.0 wt. %, on the weight of the composite, of a first alkali metal and from about 0.05 to about 10.0 wt. %, on the weight of the composite, of a second alkali metal at hydrocarbon conversion conditions. Other objects and embodiments will become evident with the following more detailed description of the invention.

DETAILED DESCRIPTION OF THE INVENTION

To summarize, the present invention is an improved catalytic composite, method of making the same as well as a process for the use thereof. Of particular interest is the use of the catalyst of the present invention as a dehydrogenation catalyst.

As indicated above, one feature of the catalyst of the invention is a platinum group component. The platinum group component may be selected from the group consisting of platinum, palladium, iridium, rhodium, osmium, ruthenium or mixtures thereof. Platinum, however, is the preferred platinum group component. It is believed that substantially all of the platinum group component exists within the catalyst in the elemental metallic state.

Preferably the platinum group component is well dispersed throughout the catalyst. The platinum group component generally will comprise about 0.01 to 5 wt. %, calculated on an elemental basis, of the final catalytic composite. Preferably the catalyst comprises about 0.1 to 2.0 wt. % platinum group component, especially about 0.1 to about 2.0 wt. % platinum component.

The platinum group component may be incorporated in the catalytic composite in any suitable manner such as, for example, by coprecipitation or cogelation, ion exchange or impregnation, or deposition from a vapor phase or from an atomic source or by like procedures either before, while or after other catalytic components are incorporated. The preferred method of incorporating the platinum group component is to impregnate the carrier material with a solution or suspension of a decomposable compound of a platinum group metal. For example, platinum may be added to the support by commingling the latter with an aqueous solution of chloroplatinic acid. Another acid, for example, nitric acid or other optional components may be added to the impregnating solution to further assist in dispersing or fixing the platinum group component in the final catalyst composite.

Regarding the Group IVA component, it may be selected from the group of germanium, tin, lead or mixtures thereof. Tin, however, is the preferred Group IVA component. We believe the Group IVA component exists within the catalyst in an oxidation state above that of the elemental metal. The Group IVA component may be present as a compound such as the oxide, for example, or combined with the carrier material or with the other catalytic components. Preferably the Group IVA component is well dispersed throughout the catalyst. The Group IVA component generally will comprise about 0.01 to 5 wt. %, calculated on an elemental basis, of the final catalyst composite. Preferably the catalyst comprises about 0.2 to about 2.0 wt. % Group IVA component, especially about 0.2 to about 2.0 wt. % tin.

The Group IVA component may be incorporated in the catalytic composite in any suitable manner such as, for example, by coprecipitation or cogelation, ion exchange or impregnation or by like procedures either before, while or after other catalytic components are incorporated. A preferred method of incorporating the tin component is cogelling it during preparation of the porous carrier material. For example, tin may be incorporated in an alumina carrier material by mixing a soluble tin compound such as stannous or stannic chloride with an alumina hydrosol, adding a gelling agent such as hexamethylenetetramine and dropping the mixture into an oil bath to form spheres containing alumina and tin. A preferred method of incorporating the germanium component is to impregnate the carrier material with a solution or suspension of a decomposable compound of germanium such as germanium tetrachloride dissolved in an alcohol. Likewise, the lead component may be impregnated from a solution of lead nitrate in water.

Regarding the alkali component the first and second alkali metal may be selected from the group consisting of cesium, rubidium, potassium, sodium and lithium; lithium as the first alkali metal, and potassium as the second alkali metal, however, are preferred. We believe that the alkali component exists in the final catalytic composite in an oxidation state above that of the elemental metal. The alkali component may be present as a compound such as the oxide, for example, or combined with the carrier material or with the other catalytic components.

Preferably the alkali component is well dispersed throughout the catalytic composite. The alkali or alkaline earth component generally will comprise from about 0.05 to about 2.0 wt. % of the first alkali metal, and from about 0.05 to about 10.0 wt. % of the second alkali metal, calculated on an elemental basis, of the final catalytic composite. Preferably the catalyst comprises from about 0.05 to about 2.0 wt. % lithium and from about 0.05 to about 3.0 wt. % potassium. Preferably, the molar ratio of potassium to platinum is at least about 10:1 and the molar ratio of potassium to lithium is at least about 0.30:1.

The alkali component may be incorporated in the catalytic composite in any suitable manner such as, for example. by coprecipitation or cogelation, by ion exchange or impregnation, or by like procedures either before, while or after other catalytic components are incorporated. A preferred method of incorporating the alkali component is to impregnate the carrier material with a solution of potassium chloride and lithium nitrate. Lithium chloride may also be used.

Regarding the porous carrier material, it is preferably a porous, absorptive support with high surface area of from about 5 to about 500 m²/g. The porous carrier material should be relatively refractory to the conditions utilized in the hydrocarbon conversion process. It is intended to include within the scope of our invention the use of carrier materials which have traditionally been utilized in hydrocarbon conversion catalysts such as, for example; (1) activated carbon, coke, or charcoal; (2) silica or silica gel, silicon carbide, clays, and silicates, including synthetically prepared and naturally occurring ones, which may or may not be acid treated, for example, attapulgus clay, china clay, diatomaceous earth, fuller's earth, kaolin, kieselguhr, etc.; (3) ceramics, porcelain, crushed firebrick, bauxite; (4) refractory inorganic oxides such as alumina, titanium dioxide, zirconium dioxide, chromium oxide, beryllium oxide, vanadium oxide, cerium oxide, hafnium oxide, zinc oxide, magnesia, boria, thoria, silica-alumina, silica-magnesia, chromia-alumina, alumina-boria, silica-zirconia, etc.; (5) crystalline zeolitic aluminosilicates such as naturally occurring or synthetically prepared mordenite and/or faujasite, for example, either in the hydrogen form or in a form which has been exchanged with metal cations, (6) spinels such as $MgAl_2O_4$, $FeAl_2O_4$, $ZnAl_2O_4$, $CaAl_2O_4$, and other like compounds having the formula $MO-Al_2O_3$ where M is a metal having a valence of 2; and (7) combinations of materials from one or more of these groups. The preferred carrier material for our catalyst is alumina, especially gamma- or eta-alumina.

The preferred alumina carrier material may be prepared in any suitable manner from synthetic or naturally occurring raw materials. The carrier may be formed in any desired shape such as spheres, pills, cakes, extrudates, powders, granules, etc., and it may be utilized in any particle size. A preferred shape of alumina is the sphere. A preferred particle size is about 1/16 inch in diameter, though particles as small as about 1/32 inch, and smaller, may also be utilized.

To make alumina spheres aluminum metal is converted into an alumina sol by reacting it with a suitable peptizing acid and water, and then dropping a mixture of the resulting sol and a gelling agent into an oil bath to form spherical particles of an alumina gel which are easily converted into the preferred gamma- or eta-alumina carrier material by known methods including aging, drying and calcining. To make alumina cylinders, an alumina powder is mixed with water and enough of a suitable peptizing agent such as nitric acid, for example, until an extrudable dough is formed. The dough is then extruded through a suitably-sized die and cut to form extrudate particles. Other shapes of the alumina carrier material may also be prepared by conventional methods. After the alumina particles are shaped generally they are dried and calcined. The alumina carrier may be subjected to intermediate treatments during its preparation, including washing with water or a solution of ammonium hydroxide, for example, which treatments are well known in the art.

The catalytic composite of our invention may also contain a halogen component. The halogen component may be either fluorine, chlorine, bromine or iodine or mixtures thereof. Chlorine and bromine are the preferred halogen components. The halogen component is generally present, we believe, in a combined state with the porous carrier material and alkali component. Preferably the halogen component is well dispersed throughout the catalytic composite. The halogen component may comprise from more than 0.2 wt. % to about 15 wt. %, calculated on an elemental basis, of the final catalytic composite.

The halogen component may be incorporated in the catalytic composite in any suitable manner, either during the preparation of the carrier material or before, while or after other catalytic components are incorporated. For example, the alumina sol utilized to form the preferred aluminum carrier material may contain halogen and thus contribute at least some portion of the halogen content in the final catalyst composite. Also, the halogen component or a portion thereof may be added to the catalyst composite during the incorporation of the carrier material with other catalyst components, for example, by using chloroplatinic acid to impregnate the platinum component. Also, the halogen component or a portion thereof may be added to the catalyst composite by contacting the catalyst with the halogen or a compound, solution, suspension or dispersion containing the halogen before or after other catalyst components are incorporated with the carrier material. Suitable compounds containing the halogen include acids containing the halogen, for example, hydrochloric acid. Or, the halogen component or a portion therof may be incorporated by contacting the catalyst with a compound, solution, suspension or dispersion containing the halogen in a subsequent catalyst regeneration step. In the regeneration step carbon deposited on the catalyst as coke during use of the catalyst in a hydrocarbon conversion process is burned off the catalyst and the platinum group component on the catalyst is redistributed to provide a regenerated catalyst with performance characteristics much like the fresh catalyst. The halogen component may be added during the carbon burn step or during the platinum group component redistribution step, for example, by contacting the catalyst with a hydrogen chloride gas. Also, the halogen component may be added to the catalyst composite by adding the halogen or a compound, solution, suspension or dispersion containing the halogen, such as propylene dichloride, for example, to the hydrocarbon feed stream or to the recycle gas during operation of the hydrocarbon conversion process.

Optionally, the catalyst of our invention may also contain a sulfur component. Generally, the sulfur component may comprise about 0.01 to 2 wt. %, calculated on an elemental basis, of the final catalytic composite. The sulfur component may be incorporated into the catalytic composite in any suitable manner. Preferably, sulfur or a compound containing sulfur such as hydrogen sulfide or a lower molecular weight mercaptan, for example, is contacted with the catalyst composite in the presence of hydrogen at a hydrogen to sulfur ratio of about 100 and a temperature of from about 10° to about 540° C., preferably under water-free conditions, to incorporaie the sulfur component.

Optionally, the catalyst may also contain other, additional components or mixtures thereof which act alone or in concert as catalyst modifiers to improve catalyst activity, selectivity or stability. Some well-known catalyst modifiers include antimony, arsenic, bismuth, cadmium, chromium, cobalt, copper, gallium, gold, indium, iron, manganese, nickel, rhenium, scandium, silver, tantalum, thallium, titanium, tungsten, uranium, zinc, and zirconium. These additional components may be added in any suitable manner to the carrier material during or after its preparation, or they may be added in any suitable manner to the catalytic composite either before, while or after other catalytic components are incorporated.

Preferably, the catalyst of our invention is nonacidic. "Nonacidic" in this context means that the catalyst has very little skeletal isomerization activity, that is, the catalyst converts less than 10 mole % of butene-1 to isobutylene when tested at dehydrogenation conditions and, preferably, converts less than 1 mole %. The acidity of the catalyst can be decreased if necessary to make the catalyst nonacidic by increasing the amount of the alkali component within the claimed range, or by treating the catalyst with steam to remove some of the halogen component.

After the catalyst components have been combined with the porous carrier material, the resulting catalyst composite will generally be dried at a temperature of from about 100° to about 320° C. for a period of typically about 1 to 24 hours or more and thereafter calcined at a temperature of about 320° to about 600° C. for a period of about 0.5 to about 10 or more hours. Finally, the calcined catalyst composite is typically subjected to a reduction step before use in the hydrocarbon conversion process. This reduction step is effected at a temperature of about 230° to about 650° C. for a period of about 0.5 to about 10 or more hours in a reducing environment, preferably dry hydrogen, the temperature and time being selected to be sufficient to reduce substantially all of the platinum group component to the elemental metallic state.

According to one process of our invention, dehydrogenatable hydrocarbons are contacted with the catalytic composite of our invention in a dehydrogenation zone maintained at dehydrogenation conditions. This contacting may be accomplished in a fixed catalyst bed system, a moving catalyst bed system, a fluidized bed system, etc., or in a batch-type operation. A fixed bed system is preferred. In this fixed bed system the hydrocarbon feed stream is preheated to the desired reaction temperature and then passed into the dehydrogenation zone containing a fixed bed of the catalyst. The dehydrogenation zone may itself comprise one or more separate reaction zones with heating means therebetween to ensure that the desired reaction temperature can be maintained at the entrance to each reaction zone. The hydrocarbon may be contacted with the catalyst bed in either upward, downward or radial flow fashion. Radial flow of the hydrocarbon through the catalyst bed is preferred for commercial scale reactors. The hydrocarbon may be in the liquid phase, a mixed vapor liquid phase or the vapor phase when it contacts the catalyst. Preferably it is in the vapor phase.

Hydrocarbons which may be dehydrogenated include dehydrogenatable hydrocarbons having from 2 to 30 or more carbon atoms including paraffins, alkylaromatics, naphthenes and olefins. One group of hydrocarbons which can be dehydrogenated with the catalyst is the group of normal paraffins having from 2 to 30 or more carbon atoms. The catalyst is particularly useful for dehydrogenating paraffins having from 2 to 15 or more carbon atoms to the corresponding mono-olefins or for dehydrogenating mono-olefins having from 3 to 15 or more carbon atoms to the corresponding di-olefins.

Dehydrogenation conditions include a temperature of from about 400° to about 900° C., a pressure of from about 0.01 to 10 atmospheres and a liquid hourly space velocity (LHSV) of from about 0.1 to 100 hr.$^{-1}$. Generally for normal paraffins the lower the molecular weight the higher the temperature required for comparable conversion. The pressure in the dehydrogenation zone is maintained as low as practicable, consistent with equipment limitations, to maximize the chemical equilibrium advantages.

The effluent stream from the dehydrogenaticn zone generally will contain unconverted dehydrogenatable hydrocarbons, hydrogen and the products of dehydrogenation reactions. This effluent stream is typically cooled and passed to a hydrogen separation zone to separate a hydrogen rich vapor phase from a hydrocarbon rich liquid phase. Generally, the hydrocarbon rich liquid phase is further separated by means of either a suitable selective adsorbent, a selective solvent, a selective reaction or reactions or by means of a suitable fractionation scheme. Unconverted dehydrogenation hydrocarbons are recovered and may be recycled to the dehydrogenation zone. Products of the dehydrogenation reactions are recovered as final products or as intermediate products in the preparation of other compounds.

The dehydrogenatable hydrocarbons may be admixed with a diluent material before, while or after being passed to the dehydrogenation zone. The diluent material may be hydrogen, steam, methane, ethane, carbon dioxide, nitrogen, argon and the like. Hydrogen is the preferred diluent. Ordinarily, when hydrogen is utilized as the diluent it is utilized in amounts sufficient to ensure a hydrogen to hydrocarbon mole ratio of about 0.1:1 to about 40:1, with best results being obtained when the mole ratio range is about 1:1 to about 10:1. The diluent hydrogen stream passed to the dehydrogenation zone will typically be recycled hydrogen separated from the effluent from the dehydrogenation zone in the hydrogen separation zone.

Water or a material which decomposes at dehydrogenation conditions to form water such as an alcohol, aldehyde, ether or ketone, for example, may be added to the dehydrogenation zone, either continuously or intermittently, in an amount to provide, calculated on the basis of equivalent water, about 1 to about 20,000 weight ppm of the hydrocarbon feed stream. About 1 to about 10,000 weight ppm of water addition gives best results when dehydrogenating paraffins having from 6 to 30 or more carbon atoms.

To be commercially successful a dehydrogenation catalyst should exhibit three characteristics, namely high activity, high selectivity and good stability. Activity is a measure of the catalyst's ability to convert reactants into products at a specific set of reaction conditions, that is, at a specified temperature, pressure, contact time and concentration of diluent such as hydrogen, if any. For dehydrogenation catalyst activity we measured the conversion or disappearance, of paraffins in percent relative to the amount of paraffins in the feedstock. Selectivity is a measure of the catalyst's ability to convert reactants into the desired product or products relative to the amount of reactants converted. For catalyst selectivity we measured the amount of olefins in the product, in mole percent, relative to the total moles of the paraffins converted. Stability is a measure of the rate of change with time on stream of the activity and selectivity parameters—the smaller rates implying the more stable catalysts.

Since dehydrogenation of hydrocarbons is an endothermic reaction and conversion levels are limited by chemical equilibrium, it is desirable in order to achieve high conversion to operate at high temperatures and low hydrogen partial pressures. At such severe conditions it is difficult to maintain high activity and selectivity for long periods of time because undesirable side reacticns such as aromatization, cracking, isomerization and coke formation increase. Therefore, it is advantageous to have a new hydrocarbon dehydrogenation catalyst with improved activity, selectivity and stability characteristics.

The following examples are introduced to further describe the catalyst and process of the invention. The examples are intended as illustrative embodiments and should not be considered to restrict the otherwise broad interpretation of the invention as set forth in the claims appended hereto.

BRIEF DESCRIPTION OF THE DRAWING

FIG. 1 is a graph of the normal paraffin conversions in weight percent versus hours on stream of the test.

FIG. 2 is a plot of the selectivities of the catalysts in weight percent for producing normal olefins versus the normal paraffin conversion in weight percent.

FIG. 3 is a graphical representation of the conversions of normal paraffins in weight percent versus the hours on stream of tests.

FIG. 4 is a plot of the selectivities of the catalysts for the production of normal olefins represented in weight percent versus the conversion of normal paraffins in weight percent.

EXAMPLE I 30.2 g of an alumina support containing tin was impregnated with 4.6 g of a 2.54 wt. % chloroplatinic acid solution, 16.43 g of a 0.8 wt. % lithium nitrate solution, both solutions being further admixed with 1.44 g of a 71 wt. % nitric acid solution in 59.6 g of water. The catalyst was then steam-dried for 2 hours and 20 minutes and then subjected to oven drying at about 150° C. for 2 hours. The catalyst was then subjected to a heating step in air for about 2.5 hours at a temperature of about 540° C. 29.6 g of the thusly prepared composite was then further subjected to impregnation with a solution comprising about 6.7 g of a 3.4 wt. % potassium chloride solution in about 88.6 g of water. The composite was then steam-dried for 2 hours, oven-dried at 150° C. for about 2 hours and calcined at about 540° C. for 2½ hours. Thereafter the catalyst was reduced. The resulting catalyst, designated Catalyst "A," comprised about 0.39 wt. % platinum, 0.5 wt. % tin, 0.77 wt. % potassium, 0.44 wt. % lithium, and about 0.75 wt. % chloride.

EXAMPLE II

In this example a second catalyst was prepared comprising only a single alkali metal component. This catalyst was made substantially in accordance with the procedures employed in Example I above. However, the potassium impregnation step and subsequent steam-drying, oven-drying and calcination steps were omitted. Accordingly, the alkali metal component of this catalyst comprised only lithium. The catalyst of this example was designated Catalyst "B" and comprised about 0.38 wt. % platinum, 0.5 wt. % tin, 0.6 wt. % lithium, and 0.1 wt. % chloride. It should be noted that although Catalyst "B" contains a different weight percent alkali metal component than Catalyst "A" they both contain approximately the same number of moles of alkali metal component total. Catalyst "A" and "B" contain about $8.4 \times 10^{-2}$ moles and $8.5 \times 10^{-2}$ moles, respectively, of alkali metal.

EXAMPLE III

A third catalyst was prepared substantially in accordance with the procedure set forth above in Example II. Accordingly, this catalyst was not made in accordance with the invention and comprised only a single alkali metal component. The catalyst of this example was designated Catalyst "C" and comprised about 0.37 wt. % platinum, about 0.5 wt. % tin, about 0.6 wt. % lithium and about 0.1 wt. % chloride.

EXAMPLE IV

In this example a fourth catalyst was prepared substantially in accordance with the procedure set forth in Example 1. However, in this instance a solution of potassium nitrate was substituted for the potassium chloride. This fourth catalyst, designated Catalyst "D," comprised about 0.38 wt. % platinum, about 0.5 wt. % tin, about 0.76 wt. % potassium, about 0.45 wt. % lithium, and about 0.19 wt. % chlorine. Therefore, this catalyst was in accordance with the invention.

EXAMPLE V

Figure 1:
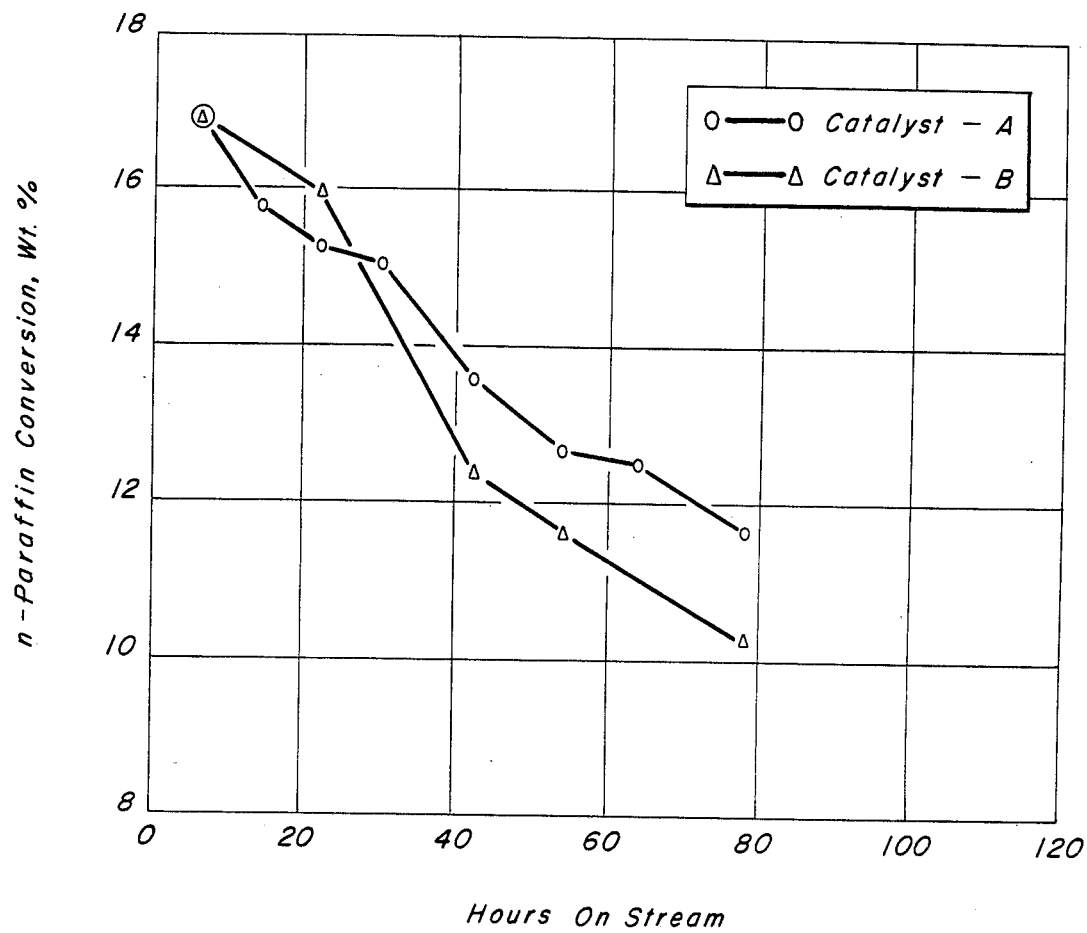
FIGS. 1 and 2 are graphical representations of the performance in the paraffin dehydrogenation process of Catalyst "A," in accordance with the invention, and Catalyst "B," different from the invention.
Figure 2:
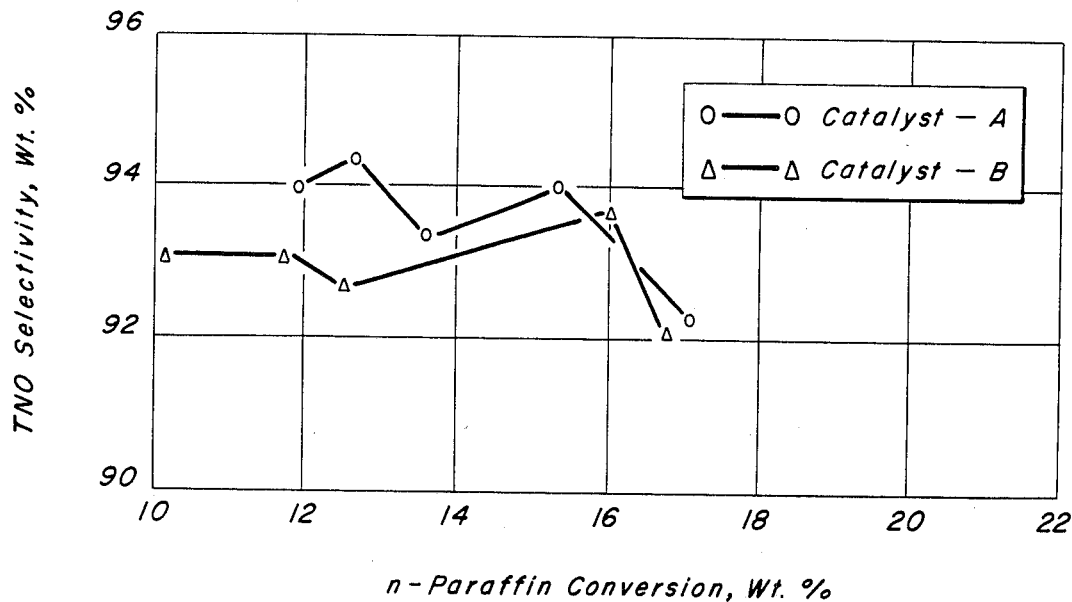

In this example Catalysts "A" and "B" were evaluated as catalysts for the dehydrogenation of normal paraffins. These evaluated tests were carried out in a pilot plant comprising a reactor and product separation facilities. The charge stock was passed into the reaction zone wherein it was contacted with 5 cc of catalyst. The effluent from the reaction zone was thereafter separated and analyzed. The charge stock comprised a mixture of $C_{10}$–$C_{13}$ normal paraffins. The reaction zone was maintained at a pressure of about 20 psig. The charge stock was passed to the reaction zone at a rate sufficient to produce a liquid hourly space velocity of about 70 hr.$^{-1}$. Hydrogen diluent was fed to the reaction zone at a rate sufficient to provide a molar hydrogen to hydrocarbon ratio of about 4:1. The feedstock was heated to a temperature of about 495° C. prior to contact with the catalyst. The results of these tests are set forth in FIGS. 1 and 2. FIG. 1 is a plot of the normal paraffin conversion in weight percent versus the number of hours on stream. The normal paraffin conversion is defined as the weight of the components in the fresh feed which actually underwent some reaction divided by the total weight of the feed. In FIG. 1 it could be seen that after 20 hours Catalyst "A" of the invention exhibited higher conversions than Catalyst "B." FIG. 2 is a plot of total normal olefin selectivity in weight percent versus the normal paraffin conversion in weight percent. The total normal olefin selectivity in weight percent is defined as the weight of charge stock components converted to the desired normal olefin product divided by the total number of charge stock components undergoing some reaction. A review of FIG. 2 discloses that Catalyst "A" of the invention showed higher or comparable selectivity for the production of desirable normal olefins than did Catalyst "B." In summary then, it can be seen that Catalyst "A" exhibited higher conversions than Catalyst "B" over the last 60 of the 80 hours of evaluation with higher selectivity for the production of the desirable normal olefins.

EXAMPLE VI

In the previous example it should be noted that Catalyst "A" comprised about 0.75 wt. % chloride while Catalyst "B" only contained 0.1 wt. % chloride. In order to substantiate that the improved performance of the catalyst of the present invention did not result from the higher halogen content of Catalyst "A" two further catalysts, Catalysts "C" and "D," were tested. As will be noted in Examples III and IV, Catalysts "C" and "D" contained about 0.1 and about 0.19 wt. % chloride, respectively. Accordingly, these catalysts contain substantially the same content of halogen.

The test procedure employed in the present invention was essentially that set forth in Example V above. However, in this case the feedstock to the process comprised $C_{11}$–$C_{13}$ normal paraffins. Addditionally the reaction zone contained a catalyst loading of 10 cc. Moreover, the catalyst was subjected to a presulfiding step having the following procedure. The catalyst was reduced in the reaction zone in flowing hydrogen at a temperature of 495° C. for 5 hours. Thereafter $H_2S$ was added to the flowing hydrogen in sufficient amount to provide a mixture of 99% hydrogen and 1% $H_2S$. This mixture was passed over the catalyst for a further period of five hours at a temperature of 495° C. After the 5 hour period the hydrogen/$H_2S$ mixture was cut and feed hydrocarbon and hydrogen diluent were cut in. The test conditions were then instituted.

Figure 3:
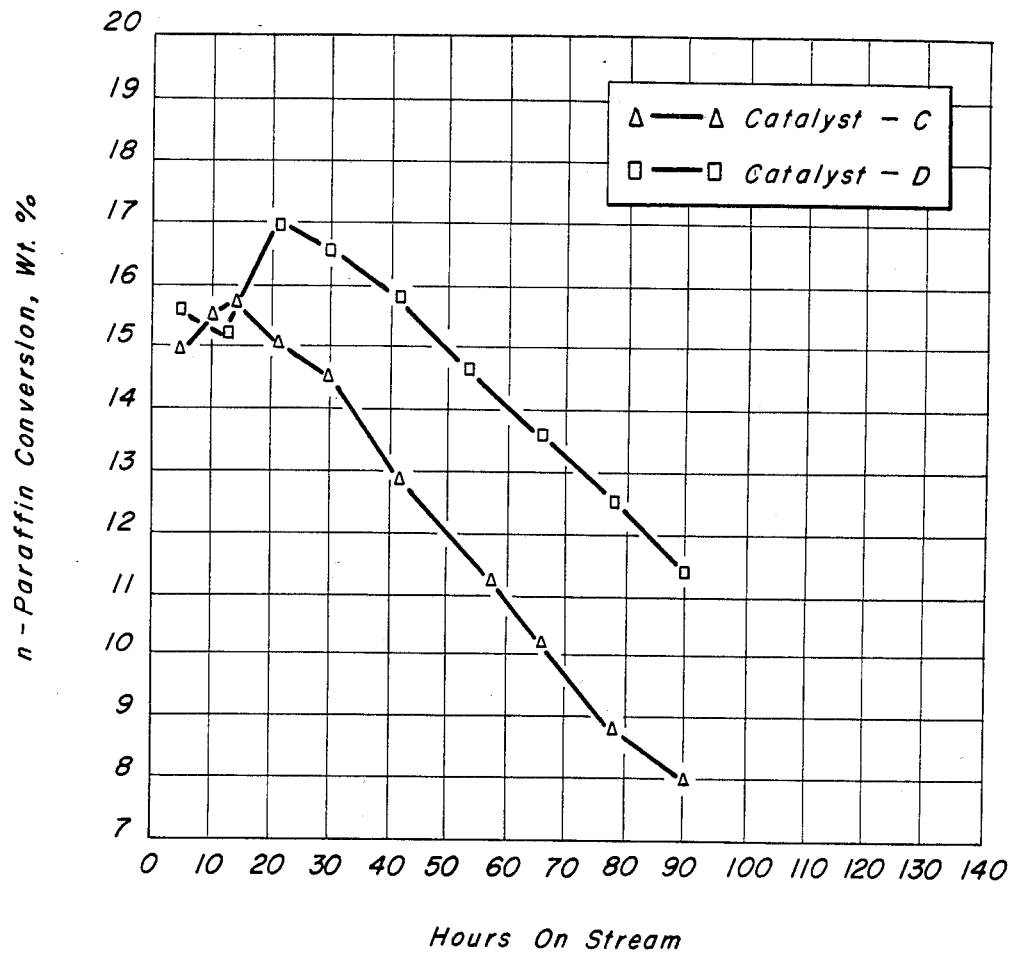
FIGS. 3 and 4 are a graphical depiction of the performance of two further catalysts in the paraffin dehydrogenation process. Depicted in these figures are Catalyst "C," different from the invention, and Catalyst "D," in accordance with the invention.
Figure 4:
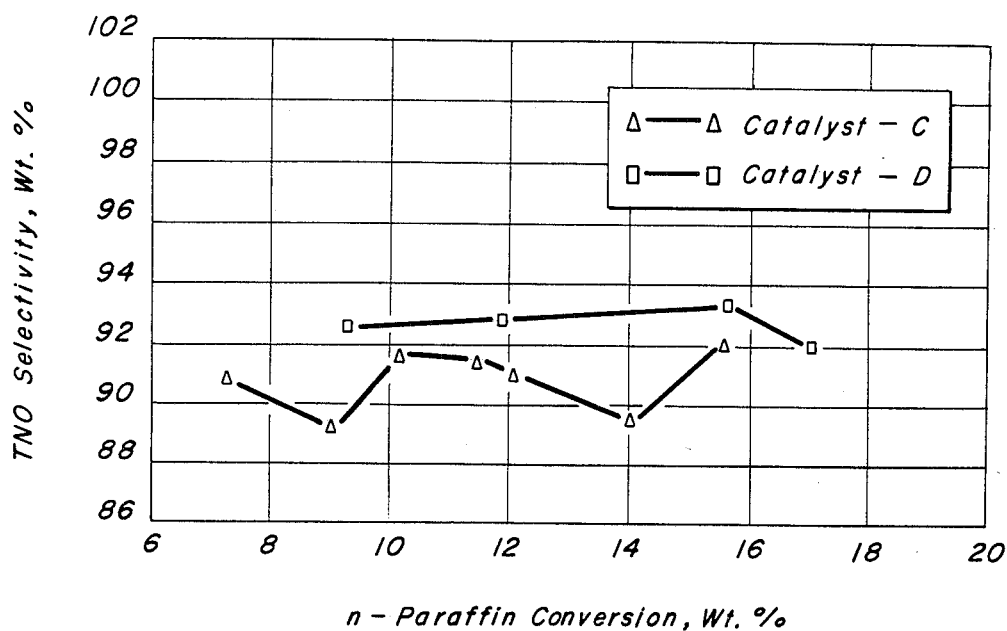

The results of testing the catalysts are set forth in FIGS. 3 and 4. FIG. 3 is a graphical representation of the conversions of normal paraffins in weight percent versus the number of hours on stream of the evaluation test. A review of FIG. 3 discloses that Catalyst "D," in accordance with the invention, exhibits higher conversions than does Catalyst "C," a catalyst different than the invention, for the last 70 hours of the 80 hour test results depicted. FIG. 4 is a graphical plot of the selectivities of the catalysts for the production of total normal olefins in weight percent versus the normal paraffin conversion in weight percent. A review of FIG. 4 discloses that Catalyst "D," in accordance with the invention, results in improved selectivity for the production of desirable normal olefins.

It can, therefore, be seen that the improved results of the catalyst of the present invention which were disclosed in Example V were not due to the halogen content difference between Catalysts "A" and "B." As disclosed in FIGS. 3 and 4, Catalyst "D," in accordance with the invention, showed superior conversion and selectivity properties to Catalyst "C" even though both had comparable halogen content.

What is claimed is:

1. A catalytic composite comprising a platinum component, a tin component and an alkali component on alumina, wherein the alkali component comprises from about 0.05 to 2.0 wt. %, on the weight of the composite, of lithium and from about 0.05 to about 3.0 wt. %, on the weight of the composite, of potassium.

2. The catalytic composite of claim 1 further characterized in that it comprises from about 0.01 to about 2.0 wt. % of the platinum component based on the weight of the composite.

3. The catalytic composite of claim 1 further characterized in that it comprises from about 0.2 to about 2.0 wt. % of the Group IVA component based on the weight of the composite.

4. The catalytic composite of claim 1 further characterized in that the carrier material comprises alumina.

5. The catalytic composite of claim 1 further characterized in that it comprises a halogen component.

6. The catalytic composite of claim 1 further characterized in that it comprises an indium component.

7. The catalytic composite of claim 1 further characterized in that is comprises a gallium component.

8. The catalytic composite of claim 1 further characterized in that it comprises a thallium component.

9. A method of preparing a catalytic composite comprising compositing a carrier material with a platinum component, a tin component, sufficient lithium to result in a lithium content of from about 0.05 to about 2.0 wt. %, based on the weight of the composite, and sufficient potassium to result in a potassium content of from about 0.05 to about 3.0 wt. %, based on the weight of the composite.

10. The method of claim 9 further characterized in that the lithium is composited by impregnation with a lithium chloride solution.

11. The method of claim 9 further characterized in that the lithium is composited by impregnation with a lithium nitrate solution.

12. The method of claim 9 further characterized in that the potassium is composited by impregnation with a potassium chloride solution.

13. The method of claim 9 further characterized in that the potassium is composited by means of a potassium nitrate solution.

14. The catalytic composite of claim 1 wherein the molar ratio of potassium to platinum is at least about 10:1.

15. The catalytic composite of claim 14 wherein the molar ratio of potassium to lithium is at least about 0.30:1.

16. The method of claim 9 wherein the molar ratio of potassium to platinum is at least about 10:1.

17. The method of claim 16 wherein the molar ratio of potassium to lithium is at least about 0.30:1.

* * * * *